US009629889B2

(12) United States Patent
Le

(10) Patent No.: US 9,629,889 B2
(45) Date of Patent: Apr. 25, 2017

(54) AQUEOUS SOLUTION FORMULATED TO RAISE BODY TEMPERATURE

(71) Applicant: Khanh Le, Madison Heights, MI (US)

(72) Inventor: Khanh Le, Madison Heights, MI (US)

( * ) Notice: Subject to any disclaimer, the term of this patent is extended or adjusted under 35 U.S.C. 154(b) by 269 days.

(21) Appl. No.: 14/520,895

(22) Filed: Oct. 22, 2014

(65) Prior Publication Data

US 2016/0113991 A1 Apr. 28, 2016

(51) Int. Cl.

| | |
|---|---|
| ***A61K 36/258*** | (2006.01) |
| ***A61K 36/54*** | (2006.01) |
| ***A61K 36/63*** | (2006.01) |
| ***A61K 36/9066*** | (2006.01) |
| ***A61K 36/185*** | (2006.01) |
| ***A61K 36/9068*** | (2006.01) |
| ***A23F 3/00*** | (2006.01) |
| ***A23L 21/25*** | (2016.01) |
| ***A23L 33/10*** | (2016.01) |
| ***A23L 33/105*** | (2016.01) |

(52) U.S. Cl.

CPC ............ *A61K 36/9068* (2013.01); *A23F 3/00* (2013.01); *A23L 21/25* (2016.08); *A23L 33/10* (2016.08); *A23L 33/105* (2016.08); *A61K 36/258* (2013.01); *A61K 36/54* (2013.01); *A61K 36/63* (2013.01)

(58) Field of Classification Search

None

See application file for complete search history.

(56) References Cited

U.S. PATENT DOCUMENTS 6,303,156 B1 * 10/2001 Ferrigno ................ A61K 33/04 128/203.16
7,201,163 B2 * 4/2007 Jiang ................ A61M 16/1075 128/200.14
2004/0235923 A1 * 11/2004 Abe ......................... A23L 2/52 514/400
2005/0021112 A1 * 1/2005 Sakamoto ............ A61F 7/0053 607/96
2006/0247310 A1 * 11/2006 Shinohara ................ A23D 9/00 514/547
2012/0276033 A1 * 11/2012 Paulsen .................... A61K 8/34 424/66

* cited by examiner

*Primary Examiner* — Chris R Tate
*Assistant Examiner* — Randall Winston
(74) *Attorney, Agent, or Firm* — Dale J. Ream

(57) ABSTRACT

An aqueous solution that is useful for helping to increase body temperature in people with chronic low body temperature, as well as people who suffer from cold hands and feet, includes a combination of ginseng, cinnamon, ginger, and jasmine tea. The body temperature raising solution may be in the form of a beverage and include a sweetener, such as honey, to improve the taste thereof. The body temperature raising solution is formulated by steeping leaves of the jasmine tea in a host liquid, suspending predetermined amounts of the ginseng, cinnamon, ginger, and honey into the host liquid, and storing the combination in an airtight container.

5 Claims, 2 Drawing Sheets

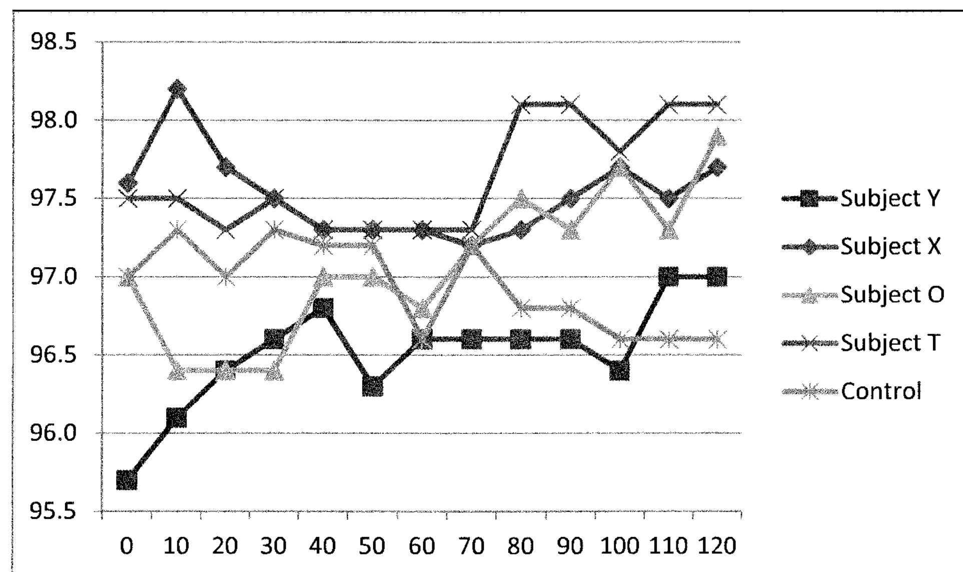
Figure 1: Core foot temperature of subjects showing foot temperatures over a 120 minute interval.
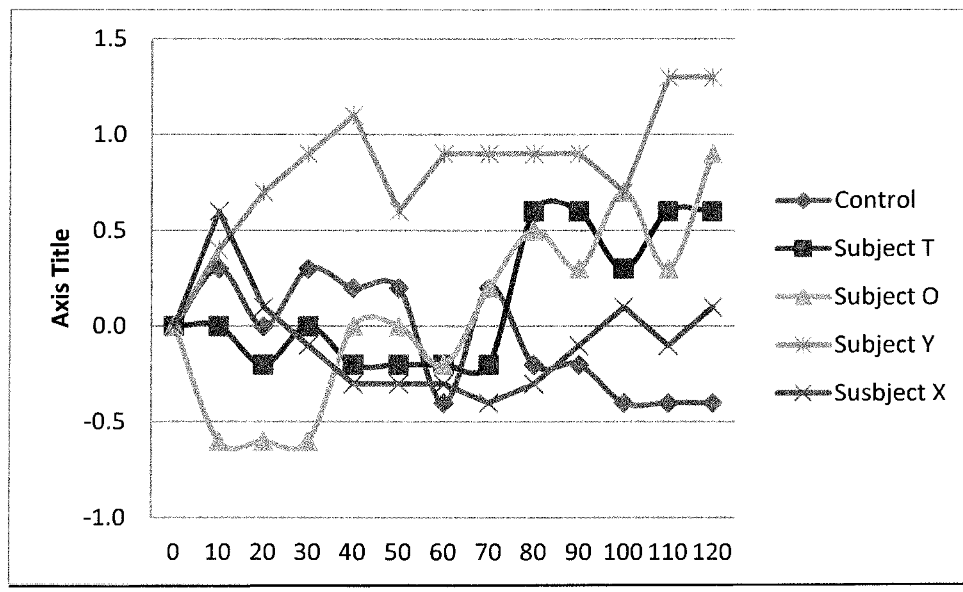
Figure 2. Core foot temperature changes of subjects taken over the course of 120 minutes.

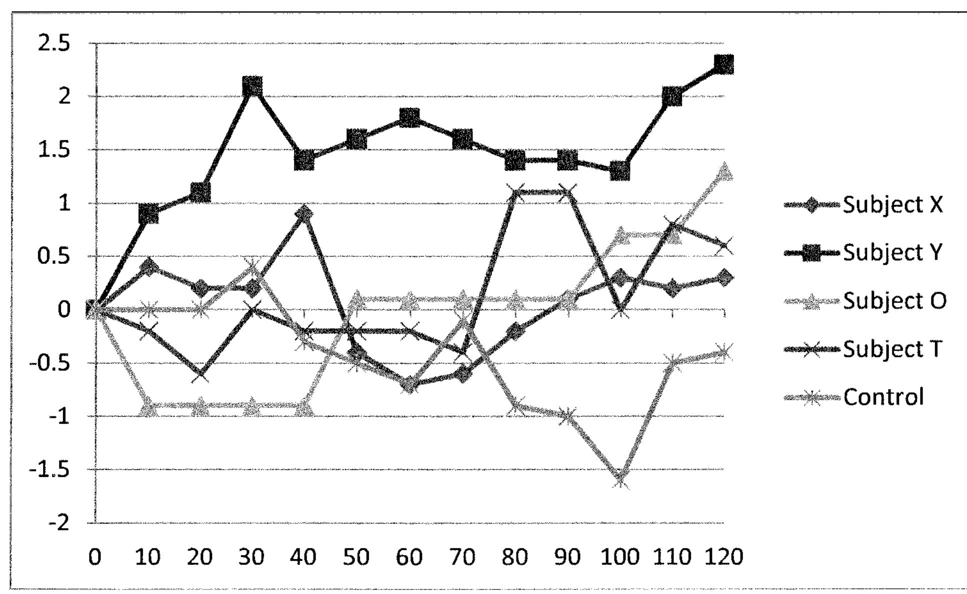
Figure 3. Core foot temperature changes of subjects taken over the course of 120 minutes.

AQUEOUS SOLUTION FORMULATED TO RAISE BODY TEMPERATURE

BACKGROUND OF THE INVENTION

This invention relates generally to an aqueous solution that may be useful for helping to increase body temperature in people with chronic low body temperature, as well as people who suffer from cold hands and feet. The aqueous solution includes a combination of ginseng, cinnamon, ginger, oxygen gas, and jasmine tea. A sweetener, such as honey, is included to enhance taste.

People living in or transplanted from very warm or even average temperature conditions often struggle to adapt to living in colder climates. For instance, a person growing up in Vietnam grows accustomed to temperatures throughout the year in the 25 degrees Celsius to 35 degrees Celsius temperature range. If such a person then moves to a colder climate, such as northern Michigan in the United States, the person may struggle to adapt to the markedly colder temperatures. More particularly, a person having difficulty becoming accustomed to a colder climate may experience cold feet, cold hands, or even a cold torso.

Various mixtures or solutions of chemical agents have been proposed in the art and prior patents for elevating a person's body temperature. Although assumably effective for their intended use, the existing proposals are directed toward medical use on patients, must be controlled in administration, and are not generally accessible to consumers.

Therefore, it would be desirable to have an aqueous solution that includes natural ingredients that may be formulated as a beverage and which may be useful for helping to increase body temperature in people with chronic low body temperature, as well as people who suffer from cold hands and feet.

SUMMARY OF THE INVENTION

Therefore, a general object of this invention is to provide an aqueous solution that is effective to increase the body temperature of a person and, particularly, in the hands and feet.

Another object of this invention is to provide a temperature modifying aqueous solution, as aforesaid, that includes a combination of ginseng, cinnamon, ginger, jasmine tea mixed in an aqueous solution with oxygen.

Still another object of this invention is to provide a temperature modifying aqueous solution, as aforesaid, that may be mixed as a beverage solution.

Yet another object of this invention is to provide a temperature modifying aqueous solution, as aforesaid, that includes a sweetener such as honey.

Accordingly, the aqueous solution described below has been shown to accomplish the objects described above.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1 is a graphical representation of a core foot temperature of subjects showing foot temperatures over a 120 minute interval;

FIG. 2 is a graphical representation of an actual rise in core foot temperature over the 120 minute interval; and FIG. 3 is a graphical representation that illustrates that at 120 minutes, each of the test subjects receiving the solution has a core foot temperature greater than that of the control, and greater than the respective starting core foot temperature.

DESCRIPTION OF THE PREFERRED EMBODIMENT

An aqueous solution formulated to raise body temperature according to a preferred embodiment of the present invention will now be described in detail with reference to FIGS. 1 to 3 of the accompanying drawings.

It is known that spices have a wide variety of uses. For example, ginseng (*Panax* sp.) is known to play a role as an aphrodisiac, a stimulant, and as an aid in the treatment of type II diabetes, among other things. Wisconsin ginseng (*Panax quinequefolius*) is especially known for its high quality, due in part to the increased amount of ginsenoside, or the active ingredient of ginseng. Cinnamon is widely used as a flavoring agent, and was historically thought to possess medicinal properties, including anti-viral, anti-bacterial, anti-fungal, and anti-inflammatory properties. Ginger is often used as a hot spice in cooking, and is also touted as having medicinal properties. More specifically, drinking ginger tea is frequently thought to help with the common cold.

The present invention broadly relates to an aqueous solution that includes a combination of ginseng, cinnamon, ginger, and jasmine tea. A sweetener, such as honey, may further be desirable. A degree of gaseous oxygen may be infused into the solution. The solution may be useful for helping to increase body temperature in people with chronic low body temperature, as well as people who suffer from cold hands and feet.

In one embodiment, the aqueous solution has about 0.5 to 1 percent by volume ginseng, about 0.5 to 1 percent by volume cinnamon, about 0.75 to 1.25 percent by volume ginger, about 0.25 to 0.5 percent by volume jasmine tea, and about 9 to 12 percent by volume honey. The remaining 84.25 to 89 percent by volume may be a hot liquid, such as (for example): water with flavoring agents and/or coloring agents, et cetera. The aqueous solution may be infused with about 7.54 to 11.27 mg/l dissolved oxygen In another embodiment, the aqueous solution has about 0.6 percent by volume ginseng, about 0.6 percent by volume cinnamon, about 0.9 percent by volume ginger, about 0.3 percent by volume jasmine tea, and about 10 percent by volume honey, with the remaining 87.6 percent by volume being a host liquid. The aqueous solution may be infused with about 7.54 mg/l dissolved oxygen. It may be particularly desirable for the ginseng to be Wisconsin ginseng.

The solution may be formulated for enteral administration (particularly for drinking) and may be heated to a desired temperature based on the personal preferences of the person consuming the drink. For example, the solution may be heated to around 85, 90, 95, 100, 105, 110, 120, or 125 degrees Fahrenheit before being consumed.

The solution is developed by first steeping tea bags or loose leaf tea with jasmine in warm water. A predetermined amount of powered ginseng, cinnamon, and ginger (e.g., in powder form) is then suspended in the water. To aid in the steeping and suspension process, it may be beneficial to heat the water to boiling for a short time (e.g., 10-15 minutes) for adding the tea, ginseng, cinnamon, and ginger. If desired, a sweeter such as honey may be added for flavor. Other sweeteners that may be used include fructose, lactose, sucralose, dextrose, saccharin, maltodextrin, pure cane sugar, processed sugar, stevia, et cetera. While any such sweetener can be used, it may be desirable for the solution to be formed of all natural ingredients. An amount of oxygen gas may be infused into the aqueous solution.

Once the components have been sufficiently combined, the solution may be allowed to cool. A person desirous of achieving an increased body temperature may drink the solution once it reaches a temperature suitable for drinking. Alternately, the solution may be stored in a container for later consumption. While the components may come out of suspension, especially with extended storage, they may become re-suspended by shaking the solution in the container. The solution may then be heated to the desired temperature and consumed.

Surprisingly, the inventive combination of ingredients, when ingested, has a synergistic effect and increases a person's body temperature for an extended period of time. As illustrated in Example 1, ingesting the solution resulted in increased body temperatures for all test subjects receiving the solution after 120 minutes had elapsed. Based on prior art beverages, test subject body temperatures would be expected to increase initially during consumption of the solution, as the solution is warmed before drinking. Temperatures would then be expected to fall as time elapsed following consumption. However, even 120 minutes after drinking the solution, the subjects surprisingly still exhibited increased body temperatures.

EXAMPLE 1

An 8 ounce solution of components in the concentrations specified below in Table 1 was administered to four test subjects of Vietnamese descent. During the test, the outside temperature was approximately 96.8 degrees Fahrenheit. Each subject's core foot temperature and foot skin temperature was taken with a thermometer, and the temperatures were recorded.

TABLE 1

Concentration of aqueous solution for increasing body temperature.

| Ingredient | Amount per 330 mL water |
|---|---|
| Ginseng | 2 g |
| Cinnamon | 2 g |
| Ginger | 3 g |
| Jasmine tea | 1 g |
| Honey | 33 g |
| Total | 41 g |

More particularly, after a 60 minute period where the subjects were required to refrain from eating or drinking, each test subject drank 8 ounces of the solution. One control subject was not given the solution. The core temperature of the subjects' feet were taken and recorded every 10 minutes for 120 minutes as shown in Table 2. FIG. 1 is a graphical representation showing that the core foot temperatures of the subjects receiving the solution were increased after 120 minutes, while the core foot temperature of the control subject was lower than the starting temperature. Table 3 shows the core foot temperature change from the original foot temperature for each subject every 10 minutes. FIG. 3 clearly shows that at 120 minutes, each of the test subjects receiving the solution have a core foot temperature greater than that of the control, and greater than the respective starting core foot temperature. The rise in core foot temperature of the subjects ranged from 0.1 to 1.3 degrees.

TABLE 2

Core foot temperature of subjects taken over the course of 120 minutes.
Core Foot Temperature

| | Subject X | Subject Y | Subject O | Subject T | Control |
|---|---|---|---|---|---|
| Temp at t = 0 | 97.6 | 95.7 | 97.0 | 97.5 | 97.0 |
| Temp at t = 10 | 98.2 | 96.1 | 96.4 | 97.5 | 97.3 |
| Temp at t = 20 | 97.7 | 96.4 | 96.4 | 97.3 | 97.0 |
| Temp at t = 30 | 97.5 | 96.6 | 96.4 | 97.5 | 97.3 |
| Temp at t = 40 | 97.3 | 96.8 | 97.0 | 97.3 | 97.2 |
| Temp at t = 50 | 97.3 | 96.3 | 97.0 | 97.3 | 97.2 |
| Temp at t = 60 | 97.3 | 96.6 | 96.8 | 97.3 | 96.6 |
| Temp at t = 70 | 97.2 | 96.6 | 97.2 | 97.3 | 97.2 |
| Temp at t = 80 | 97.3 | 96.6 | 97.5 | 98.1 | 96.8 |
| Temp at t = 90 | 97.5 | 96.6 | 97.3 | 98.1 | 96.8 |
| Temp at t = 100 | 97.7 | 96.4 | 97.7 | 97.8 | 96.6 |
| Temp at t = 110 | 97.5 | 97.0 | 97.3 | 98.1 | 96.6 |
| Temp at t = 120 | 97.7 | 97.0 | 97.9 | 98.1 | 96.6 |

TABLE 3

Core foot temperature changes of subjects taken over the course of 120 minutes.
Average Rise in Core Foot Temperature

| | Subject X | Subject Y | Subject O | Subject T | Control |
|---|---|---|---|---|---|
| Temp at t = 0 | 0.0 | 0.0 | 0.0 | 0.0 | 0.0 |
| Temp at t = 10 | 0.6 | 0.4 | −0.6 | 0.0 | 0.3 |
| Temp at t = 20 | 0.1 | 0.7 | −0.6 | −0.2 | 0.0 |
| Temp at t = 30 | −0.1 | 0.9 | −0.6 | 0.0 | 0.3 |
| Temp at t = 40 | −0.3 | 1.1 | 0.0 | −0.2 | 0.2 |
| Temp at t = 50 | −0.3 | 0.6 | 0.0 | −0.2 | 0.2 |
| Temp at t = 60 | −0.3 | 0.9 | −0.2 | −0.2 | −0.4 |
| Temp at t = 70 | −0.4 | 0.9 | 0.2 | −0.2 | 0.2 |
| Temp at t = 80 | −0.3 | 0.9 | 0.5 | 0.6 | −0.2 |
| Temp at t = 90 | −0.1 | 0.9 | 0.3 | 0.6 | −0.2 |
| Temp at t = 100 | 0.1 | 0.7 | 0.7 | 0.3 | −0.4 |
| Temp at t = 110 | −0.1 | 1.3 | 0.3 | 0.6 | −0.4 |
| Temp at t = 120 | 0.1 | 1.3 | 0.9 | 0.6 | −0.4 |

The temperature of the skin of the foot also exhibited increased temperatures. Table 4 shows the temperature changes of the skin temperature of each test subject and the control subject over 120 minutes, with the temperature being taken every 10 minutes. FIG. 3 illustrates the rise in skin temperature of the feet ranged from 0.3 degrees to 2.3 degrees.

TABLE 4

Skin foot temperature changes of subjects taken over the course of 120 minutes.
Average Rise in Skin Foot Temp

| | Subject X | Subject Y | Subject O | Subject T | Control |
|---|---|---|---|---|---|
| Temp at t = 0 | 0 | 0 | 0 | 0 | 0 |
| Temp at t = 10 | 0.4 | 0.9 | −0.9 | −0.2 | 0 |
| Temp at t = 20 | 0.2 | 1.1 | −0.9 | −0.6 | 0 |
| Temp at t = 30 | 0.2 | 2.1 | −0.9 | 0 | 0.4 |
| Temp at t = 40 | 0.9 | 1.4 | −0.9 | −0.2 | −0.3 |
| Temp at t = 50 | −0.4 | 1.6 | 0.1 | −0.2 | −0.5 |
| Temp at t = 60 | −0.7 | 1.8 | 0.1 | −0.2 | −0.7 |
| Temp at t = 70 | −0.6 | 1.6 | 0.1 | −0.4 | −0.1 |
| Temp at t = 80 | −0.2 | 1.4 | 0.1 | 1.1 | −0.9 |

TABLE 4-continued

Skin foot temperature changes of subjects taken over the course of 120 minutes.
Average Rise in Skin Foot Temp

| | Subject X | Subject Y | Subject O | Subject T | Control |
|---|---|---|---|---|---|
| Temp at t = 90 | 0.1 | 1.4 | 0.1 | 1.1 | −1 |
| Temp at t = 100 | 0.3 | 1.3 | 0.7 | 0 | −1.6 |
| Temp at t = 110 | 0.2 | 2 | 0.7 | 0.8 | −0.5 |
| Temp at t = 120 | 0.3 | 2.3 | 1.3 | 0.6 | −0.4 |

These results clearly indicate that the inventive solution successfully—and surprisingly—increases body temperature over a significant period of time when ingested.

It is understood that while certain forms of this invention have been illustrated and described, it is not limited thereto except insofar as such limitations are included in the following claims and allowable functional equivalents thereof.

The invention claimed is:

1. A method of manufacturing a solution for enteral administration comprising ginseng, cinnamon, ginger, jasmine tea, and honey, wherein the method comprises:

a) steeping leaves of the jasmine tea in water;

b) suspending predetermined amounts of the ginseng, cinnamon, ginger, and honey into the water;

c) dissolving a predetermined amount of oxygen into the water; and d) storing the combination in an airtight container, wherein the predetermined amounts are: about 0.5 to 1% by volume ginseng, about 0.5 to 1% by volume cinnamon, about 0.75 to 1.25% by volume ginger, about 9 to 12% by volume honey, and about 7.54 to 11.27 mg/I dissolved oxygen.

2. The method of claim 1, wherein the water includes at least one flavoring agent.

3. The method of claim 2, wherein the water further includes at least one coloring agent.

4. The method of claim 1, wherein the water includes at least one coloring agent.

5. The method of claim 1, wherein the predetermined amounts are: about 0.6% by volume ginseng, about 0.6% by volume cinnamon, about 0.9% by volume ginger, about 10% by volume honey, and about 7.54 mg/l dissolved oxygen.

* * * * *